United States Patent
Peng

(10) Patent No.: US 6,638,407 B1
(45) Date of Patent: Oct. 28, 2003

(54) ELECTROCHEMICAL GAS SENSOR WITH GAS COMMUNICATION MEANS

(75) Inventor: Wenfeng Peng, North York (CA)

(73) Assignee: Senco Sensors Inc., Vancouver (CA)

( * ) Notice: Subject to any disclaimer, the term of this patent is extended or adjusted under 35 U.S.C. 154(b) by 0 days.

(21) Appl. No.: 09/952,227

(22) Filed: Sep. 13, 2001

Related U.S. Application Data

(63) Continuation of application No. 09/417,443, filed on Oct. 13, 1999, now abandoned.

(30) Foreign Application Priority Data

Oct. 12, 1998 (CA) .............................................. 2255472

(51) Int. Cl.⁷ ........................ G01N 27/26; G01N 27/404
(52) U.S. Cl. ........................ 204/432; 204/412; 204/415; 204/431
(58) Field of Search ................................. 204/412, 415, 204/431, 432

(56) References Cited

U.S. PATENT DOCUMENTS

| | | | |
|---|---|---|---|
| 3,929,603 A | * | 12/1975 | Porter |
| 4,141,800 A | * | 2/1979 | Breuer et al. |
| 4,172,770 A | * | 10/1979 | Semersky et al. |
| 4,455,213 A | * | 6/1984 | Neti et al. |
| 4,587,003 A | * | 5/1986 | Tantram et al. |
| 5,250,171 A | * | 10/1993 | Warburton et al. |
| 5,284,566 A | * | 2/1994 | Cuomo et al. |
| 5,338,429 A | * | 8/1994 | Jolson et al. |
| 5,395,507 A | * | 3/1995 | Aston et al. |
| 5,632,875 A | * | 5/1997 | Chapples et al. |
| 5,635,627 A | * | 6/1997 | Bytyn |
| 5,879,527 A | * | 3/1999 | Kiesele et al. |

* cited by examiner

Primary Examiner—T. Tung
(74) Attorney, Agent, or Firm—Libert & Associates; Victor E. Libert

(57) ABSTRACT

An electrochemical sensor having electrolyte, at least two electrodes and an electrolyte reservoir in a housing. The sensor has a hydrophobic gas communication means between said electrodes, electrolyte reservoir and ambient atmosphere. An electrochemical sensor having hydrophobic communication means mounted between electrodes and extending down to the electrolyte reservoir of the electrochemical sensor. Either embodiment of the sensor can provide oxygen for operation of the sensor and a balance of pressure, without interfering or poisonous gases.

13 Claims, 3 Drawing Sheets though the gas (carbon monoxide) concentration remains unchanged. In a three-electrode sensor, the oxygen is reduced to water at the counter electrode. In a two-electrode sensor, oxygen is reduced at the counter electrode, which also serves as a reference electrode.

ELECTROCHEMICAL GAS SENSOR WITH GAS COMMUNICATION MEANS

CROSS-REFERENCE TO RELATED APPLICATION

This application is a continuation of application Ser. No. 09/417,443, filed Oct. 13, 1999, now abandoned

FIELD OF THE INVENTION

The present invention relates to an electrochemical gas sensor having electrolyte and at least two electrodes, in which there is a hydrophobic gas communication means between the electrodes, extending to the electrolyte reservoir of the electrochemical sensor, and especially extending between the electrode and the ambient atmosphere. In particular, the electrochemical sensor uses an air/platinum electrode and an acidic electrolyte, especially sulphuric acid.

BACKGROUND OF THE INVENTION

Most amperometric electrochemical sensors employ an air/platinum electrode as the reference electrode. Thus, the output from the sensor depends significantly on the potential of this reference electrode. If the reference electrode maintains a constant potential, the sensor will give a stable output that is linear with the concentration of the gas that is to be detected e.g. carbon monoxide.

The potential of the reference electrode is determined by the concentration of hydrogen ions and the partial pressure of oxygen. Any change in the concentration or partial pressure will cause a drift in the output of the sensor in the presence of, for example, carbon monoxide if carbon monoxide is the target gas that is to be detected. If, for example, oxygen is depleted around the reference electrode, the output of the sensor would drop to zero even though the gas (carbon monoxide) concentration remains unchanged. In a three-electrode sensor, the oxygen is reduced to water at the counter electrode. In a two-electrode sensor, oxygen is reduced at the counter electrode, which also serves as a reference electrode.

Buildup of pressure inside a sensor is another problem. Many sensors use an acidic electrolyte combined with a reservoir that is partially filled with electrolyte. Consequently, there is a substantial amount of air in the reservoir, which is separated from the ambient atmosphere by the electrolyte. This liquid-trapped air expands when subjected to elevated temperature, or becomes compressed when the volume of electrolyte increases due to the absorption of water from a humid atmosphere. As it is very difficult for air to dissolve in an aqueous electrolyte, the air pressure inside the sensor increases. A large pressure difference across the sensing electrode can cause leakage of electrolyte either through the sensing electrodes membrane, or through the joints between the parts of the housing in which the sensor is located.

U.S. Pat. No. 4,587,003 discloses the use of both hydrophobic and hydrophobic paths in a sensor for detection of, for example, carbon monoxide, to overcome problems associated with interfering gases contacting the sensing electrode by permitting the interfering gas to also contact the counter electrode. The patent discloses the use of several capillary holes each of a diameter of about 2 mm filled with hydrophobic material in a hydrophilic matrix between the electrodes, and the use of Teflon™-impregnated fiber glass pads.

In some other sensors, the dosage of electrolyte is strictly controlled so that the adsorbent matrix is not completely saturated with electrolyte and oxygen is supplied to the reference/counter electrode(s) through these dry regions.

Sensors made by these methods have the drawback of difficulty in matrix preparation and unreliable sensor performance. For example, a sensor using a partially dry matrix absorbs water when subjected to high humidity. Consequently, the dry areas can become wet and the gas channel eliminated, with the consequence that the output of the sensor will decrease over a period of time in a target gas e.g. carbon monoxide, due to decreasing partial pressure of oxygen.

To facilitate equalization of pressures inside and outside a sensor, and provide an oxygen path to the electrolyte, U.S. Pat. No. 5,284,566 and U.S. Pat. No. 5,338,429 disclose the use of a small hole in the bottom of a sensor body which is covered by a piece of gas porous but liquid impervious material. Such a design has serious disadvantages. In addition to possible leakage through this hole and increased manufacturing cost, the gas pathway can easily be flooded by electrolyte even when the sensor is sitting in an upright position. Moreover, it provides a passage for a target gas e.g. carbon monoxide, to access the reference electrode by diffusion, causing a drift in the reference electrode potential and a decrease in sensor output. If a poisoning gas enters the sensor, the life and performance of the sensor will be affected.

Alternate methods of ensuring adequate supply of oxygen and for prevention of pressure buildup within a sensor are required.

SUMMARY OF THE INVENTION

An electrochemical gas sensor in which hydrophobic means are provided for transmission of oxygen within the sensor and for relief of pressure has now been found.

Accordingly, one aspect of the present invention provides an electrochemical gas sensor having electrolyte, at least two electrodes and an electrolyte reservoir, said electrolyte reservoir containing electrolyte, said electrodes and electrolyte being contained in a housing, said sensor having a hydrophobic gas communication means between said electrodes, electrolyte reservoir and ambient atmosphere.

In an preferred embodiment of the present invention, the hydrophobic gas communication means facilitates equalization of pressure inside the sensor with atmospheric pressure.

In a further embodiment of the invention, the hydrophobic gas communication means provides for transmission of oxygen to electrodes, especially to the reference electrode and counter electrode.

Another aspect of the present invention provides an electrochemical gas sensor having hydrophobic gas communication means, said electrochemical sensor having electrodes and an electrolyte reservoir, said hydrophobic communication means being mounted between the electrodes and extending down to the electrolyte reservoir of the electrochemical sensor.

BRIEF DESCRIPTION OF THE DRAWINGS

The present invention is illustrated by the embodiments shown in the drawings, in which.

DETAILED DESCRIPTION OF THE INVENTION

Figure 1:
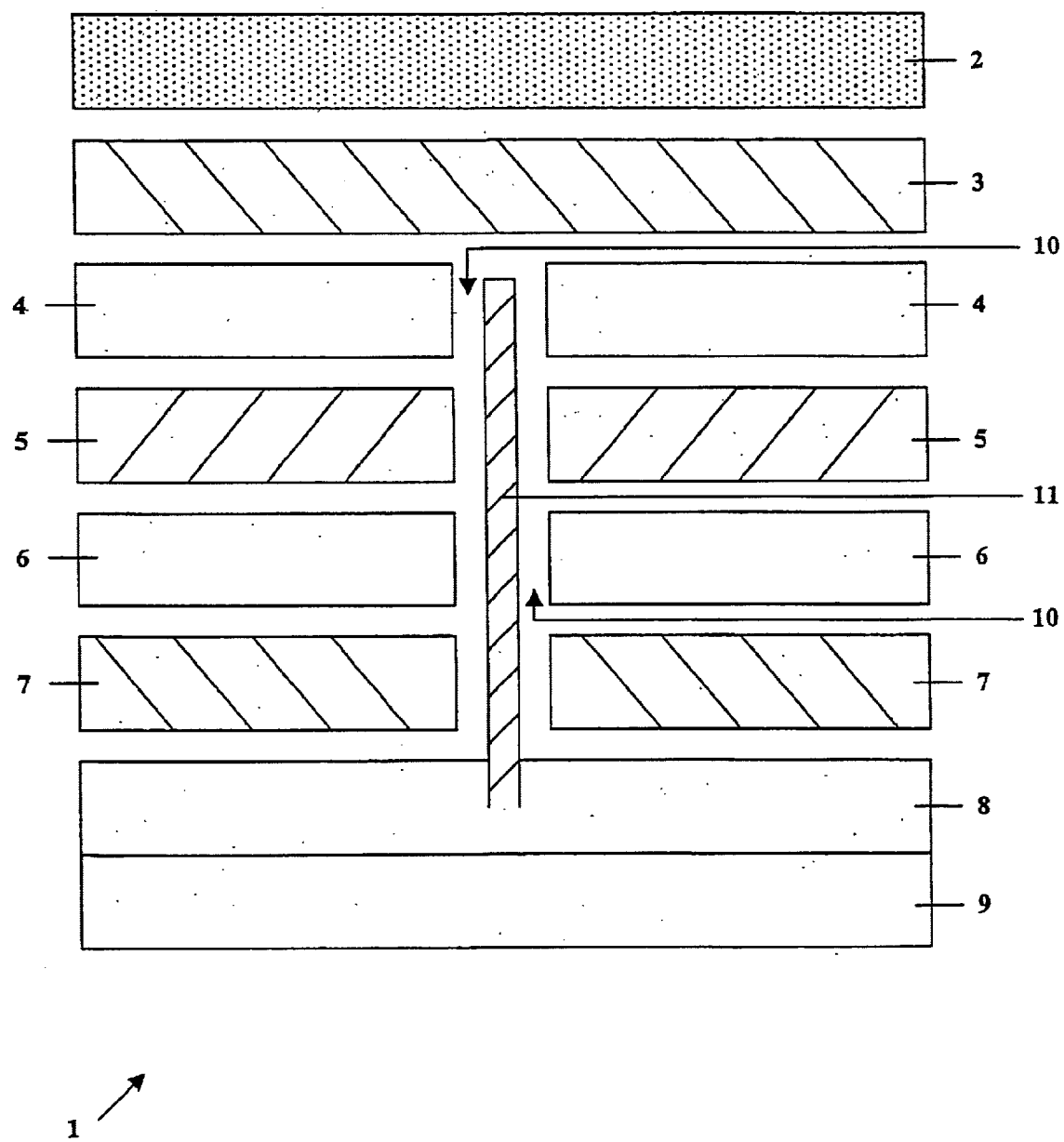
FIG. 1 is schematic representation of a three electrode sensor with gas communication means.

FIG. 1 shows a three-electrode sensor, generally indicated by 1. Three-electrode sensor 1 has a gas filter 2, a sensing electrode 3, a first matrix 4, a reference electrode 5, a second matrix 6, a counter electrode 7 and a reservoir with air 8 and electrolyte 9. It is understood that the sensor would have a housing surrounding the electrodes and reservoir. It is preferred that the electrodes described herein be gas porous or gas permeable electrodes.

It will be noted that reference electrode 5 and counter electrode 7 are annular i.e. there is a central orifice 10 in those electrodes. Similarly, first matrix 4 and second matrix 6 have a corresponding orifice.

A gas communication means 11 extends down orifice 10 from first matrix 4 through counter electrode 7 and into air 8 in the electrolyte reservoir. Thus, there is gas communication between sensing electrode 3 and the reservoir.

Figure 2:
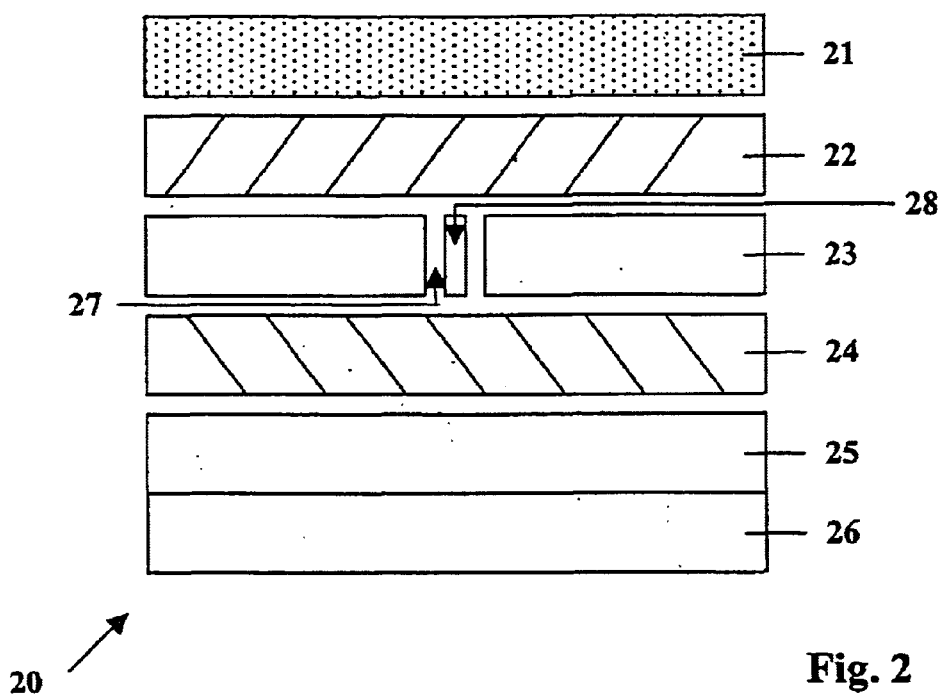
FIG. 2 is a schematic representation of a two-electrode sensor with gas communication means.

FIG. 2 shows a two-electrode sensor, generally indicated by 20. Two-electrode sensor 20 has gas filter 21, sensing electrode 22, matrix 23, counter electrode 24 and air 25 and electrolyte 26 in a reservoir. Matrix 23 is annular with an orifice 27 therein. Orifice 27 has gas communication means 28 located therein to provide gas communication between counter electrode 24 and sensing electrode 22.

Figure 3:
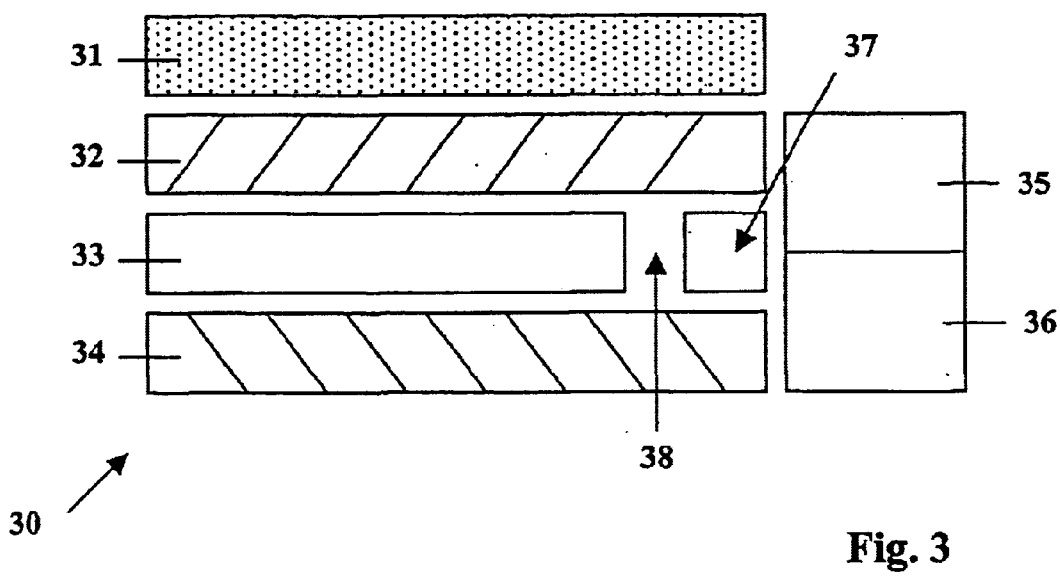
FIG. 3 is schematic representation of a two-electrode sensor with alternate gas communication means.

FIG. 3 shows a two-electrode sensor, generally indicated by 30. Two-electrode sensor 30 has gas filter 31, sensing electrode 32, matrix 33 and counter electrode 34. In this embodiment, the air and electrolyte of the reservoir, indicated by 35 and 36 respectively, are located to the side of the electrodes, rather than beneath the electrodes as shown in FIG. 2. Gas communication means 37 is located in an orifice 38 that is on one side of or around matrix 33.

The sensor of the present invention has gas channels throughout the sensor. These gas channels ensure a balanced pressure inside the sensor, and a continuous supply of oxygen for the operation of air/platinum reference and counter electrodes. The gas channels are created by using hydrophobic materials, which must be inert with respect to the electrolyte. Examples of the hydrophobic materials include porous polytetraftuoroetbylene, e.g., Teflon™ polymer, which remain dry when surrounded by electrolyte.

The issue of stability of output of the sensor is accomplished by establishing a permanent gas communication means between the sensing electrode and reference electrode. For example, a 1–3 mm wide, 1 cm long Teflon ribbon cut from normal 0.001 inch thick Teflon sealing tape can be pressed together with both electrodes to meet this requirement. In such an embodiment, the gas communication means will not break even though the sensing electrode may flex.

The gas communication means is further extended to the electrolyte reservoir, preferably to the area where air is most likely to occur. Thus, any pressure caused by extreme environmental changes e.g. high humidity, high temperature, can be alleviated or released by means of such a gas communication means.

Figure 4:
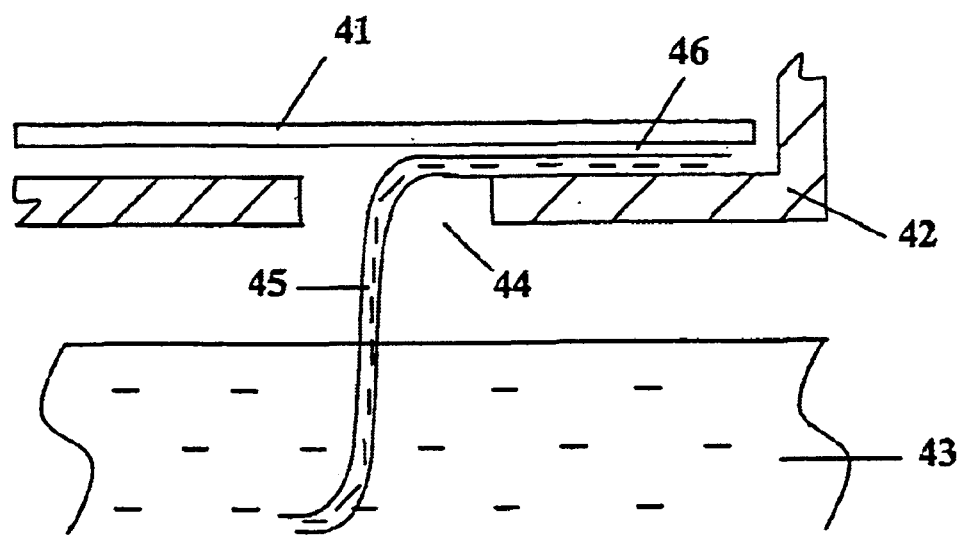
FIG. 4 is a schematic representation of a partial section of a two-electrode sensor with an embodiment of a gas communication means.

It is not essential that the gas communication means in the electrolyte reservoir be a physical part of the electrodes if assembly of the sensor is found to be accomplished more conveniently in some other way. For example, in a two-electrode sensor there can be a small opening e.g. about 1–3 mm, in the reference/counter electrode support. In order to prevent it from being blocked by electrolyte, a small piece of Teflon tape or a small strip cut from porous Teflon membrane is inserted through this opening. Such a piece of hydrophobic material should have a length that is longer than or about the depth of the electrolyte reservoir and is secured in place by bending the top end and sandwiching it with the reference electrode and the reference electrode support. A sensor built in this way has a balanced pressure, even when the sensor is put in an upside down position. One embodiment of such a gas communication means is shown in FIG. 4. FIG. 4 shows a partial section of a two-electrode sensor, 40, having a reference/counter electrode 41 on a support 42. Support 42 is spaced from electrolyte 43, with air 46 in between. Support 42 is shown as having an orifice 44 therein, through which a piece of hydrophobic material 45 passes. Hydrophobic material 45 extends from electrolyte 43, through orifice 44 in support 42 and is held in place between reference/counter electrode 41 and an upper surface of support 42.

In another embodiment of a two electrode sensor, when the reference electrode has a thick Teflon backing layer, there would be no need for a solid support. Alternatively, a widely open reference electrode support could be used. In other embodiments of the invention, Teflon ribs or crosses could be used and/or additional Teflon membranes could be placed under the reference electrode. In all cases, the reference electrode is in gas communication with the ambient atmosphere and is open to the air in the electrolyte reservoir.

With the gas communication means extending down to the reservoir, the sensing electrode will not become stressed convex under normal operating conditions. However the electrode may flex in either convex or concave manner during preparation. In order to prevent it from deforming, a firm porous, activated carbon impregnated filter or a gas filter of another type may be mounted on top of the sensing electrode. Such a gas filter absorbs, or removes, interfering and poisoning gases before entering the sensor, and directs the gas of interest uniformly over the entire electrode surface.

In particular embodiments, the present invention provides a hydrophobic gas communication means that is mounted between electrodes and extends down to the electrolyte reservoir in an electrochemical sensor, providing oxygen for the operation of the reference electrode and balancing the air pressure inside and outside the sensor. The gas communication means in the reservoir is an integral part between the electrodes, although it may be physically separated. If two separate gas communication means are used, they may be connected through gas porous electrodes. In preferred embodiments, the gas communication means is connected to the sensing electrode and gases that diffuse through this gas communication means come from the air that has passed the sensing electrode on which the target gas e.g. carbon monoxide, is converted and detected. The area that the gas communication means contacts the sensing electrode should be minimized, so that most of the target gas, if not all, has been converted in the air that diffuses through this gas communication means. In the case of a large contact area, it's possible that the target gas enters the sensor without undergoing an electrochemical reaction on the sensing electrode due to a lack-of electrolyte in that specific area. In further preferred embodiments, the gases that diffuse through the communication means come from the air that has passed a gas filter mounted in a gas inlet of the sensor. Interfering and poisonous gases are removed by the gas filter.

What is claimed is:

1. An electrochemical gas sensor having an electrolyte matrix, a sensing electrode and a second electrode sandwiching the matrix, and an electrolyte reservoir, said electrolyte reservoir containing electrolyte, said electrodes and electrolyte being contained in a housing such that the sensing electrode is in gas communication with the atmosphere, said sensor having a hydrophobic gas communication channel connected to and extending continuously between the sensing electrode and inside the reservoir thereby facilitating equalization of pressure inside the reservoir with atmospheric pressure.

2. The electrochemical sensor of claim 1 in which the hydrophobic gas communication channel is in gas communication with the electrodes thereby providing for transmission of oxygen from the atmosphere to the electrodes.

3. The electrochemical sensor of claim 1 in which the matrix and the second electrode each comprise an orifice for flowthrough of electrolyte, and the gas communication channel extends through the matrix and second electrode orifices and is in gas communication with the reservoir, sensing electrode, electrolyte matrix and the second electrode.

4. An electrochemical gas sensor having hydrophobic gas communication means, said electrochemical sensor having a sensing electrode and a second electrode sandwiching an electrolyte matrix, and an electrolyte reservoir for containing electrolyte, said sensing electrode being in gas communication with the atmosphere, and said hydrophobic communication means being connected to and extending continuously between the sensing electrode and inside the reservoir thereby facilitating equalization of pressure inside the reservoir with atmospheric pressure.

5. The electrochemical sensor of claim 4 in which the hydrophobic gas communication means is in gas communication with the second electrode and thereby provides for oxygen to diffuse to the second electrode in the sensor and for balancing of air pressure between the inside and outside of the sensor.

6. The electrochemical sensor of claim 5 in which the reservoir is located beside the electrodes.

7. The electrochemical sensor of claim 5 in which the reservoir is physically separated from the electrodes.

8. The electrochemical sensor of claim 5 in which the gas communication means comprises a hydrophobic gas channel connected at one end to a hydrophobic portion of the sensing electrode and the other end to a hydrophobic portion of the second electrode, and a hydrophobic strip attached to the hydrophobic portion of the second electrode and extending into the reservoir.

9. The electrochemical sensor of claim 5 in which the gas communication means is dimensioned and configured so that gases that diffuse through the gas communication means come from the air that has passed the sensing electrode.

10. The electrochemical sensor of claim 5 further comprising a housing containing the electrodes, electrolyte matrix and gas communication means, the housing comprising a gas inlet that provides gas communication between the sensing electrode and the atmosphere and a gas filter mounted in the gas inlet.

11. The electrochemical sensor of claim 10 adapted so that diffusion of gas through the gas communication means is from air that has passed through the gas filter.

12. The sensor of claim 4 in which the second electrode is a counter electrode.

13. The sensor of claim 4 in which the second electrode is a reference electrode and the sensor further comprises a counter electrode and a second electrolyte matrix sandwiched between the reference electrode and the counter electrode.

* * * * *